United States Patent
Pan et al.

(10) Patent No.: US 9,925,130 B2
(45) Date of Patent: Mar. 27, 2018

(54) COMPOSITION WITH ZINC AMINO ACID/TRIMETHYLGLYCINE HALIDE PRECURSORS

(71) Applicant: Colgate-Palmolive Company, Piscataway, NJ (US)

(72) Inventors: Long Pan, Cherry Hill, NJ (US); Jairajh Mattai, Piscataway, NJ (US); Shamim Ansari, Princeton, NJ (US); Jianhong Qiu, Green Brook, NJ (US); James G. Masters, Ringoes, NJ (US); Ying Yang, Monmouth Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 45 days.

(21) Appl. No.: 14/653,308

(22) PCT Filed: Dec. 19, 2012

(86) PCT No.: PCT/US2012/070492
§ 371 (c)(1),
(2) Date: Jun. 18, 2015

(87) PCT Pub. No.: WO2014/098814
PCT Pub. Date: Jun. 26, 2014

(65) Prior Publication Data
US 2015/0328095 A1 Nov. 19, 2015

(51) Int. Cl.
*A61K 8/27* (2006.01)
*A61K 8/20* (2006.01)
*A61K 8/44* (2006.01)
*A61Q 15/00* (2006.01)
*A61Q 17/00* (2006.01)
*A61Q 19/00* (2006.01)
*A61Q 19/10* (2006.01)
*A61Q 5/00* (2006.01)
*A61Q 5/02* (2006.01)
*A61Q 5/12* (2006.01)

(52) U.S. Cl.
CPC ............... *A61K 8/27* (2013.01); *A61K 8/20* (2013.01); *A61K 8/44* (2013.01); *A61Q 5/00* (2013.01); *A61Q 5/02* (2013.01); *A61Q 5/12* (2013.01); *A61Q 15/00* (2013.01); *A61Q 17/005* (2013.01); *A61Q 19/00* (2013.01); *A61Q 19/10* (2013.01); *A61K 2800/58* (2013.01)

(58) Field of Classification Search
CPC ... A61K 8/27; A61K 8/20; A61K 8/44; A61K 2800/58; A61Q 15/00; A61Q 19/00; A61Q 10/00; A61Q 5/00; A61Q 5/02; A61Q 5/12; A61Q 17/005
See application file for complete search history.

(56) References Cited

U.S. PATENT DOCUMENTS

| | | | |
|---|---|---|---|
| 2,503,280 A | 4/1950 | Lockwood |
| 2,507,088 A | 5/1950 | Bradley |
| 2,527,686 A | 10/1950 | Sandberg |
| 2,893,918 A | 7/1959 | Abramson |
| 3,260,744 A | 7/1966 | Kenkichi |
| 3,320,174 A | 5/1967 | Rubinfeld |
| 3,372,188 A | 3/1968 | Terence |
| 3,535,421 A | 10/1970 | Briner |
| 3,538,230 A | 11/1970 | Morton |
| 3,678,154 A | 7/1972 | Briner |
| 3,741,911 A | 6/1973 | Shane |
| 3,862,307 A | 1/1975 | Giulio |
| 3,937,807 A | 2/1976 | Haefele |
| 3,941,818 A | 3/1976 | Abdel-Monem |
| 3,959,458 A | 5/1976 | Agricola et al. |
| 4,051,234 A | 9/1977 | Gieske et al. |
| 4,316,824 A | 2/1982 | Pancheri |
| 4,339,432 A | 7/1982 | Ritchey et al. |
| 4,340,583 A | 7/1982 | Wason |
| 4,487,757 A | 12/1984 | Kiozpeoplou |
| 4,565,693 A | 1/1986 | Marschner |

(Continued)

FOREIGN PATENT DOCUMENTS

| CN | 1494896 A | 5/2004 |
|---|---|---|
| CN | 101606639 | 12/2009 |

(Continued)

OTHER PUBLICATIONS

Anonymous, "Zinc Lauryl Ether Sulphate, A New Approach to Skincare,", Apr. 2004, Retrieved from Internet, http://www.erwebhosting.it/zsi/repository/Zinc%20Lauryl%20Ether%20Sulphate,%20A%20new%20approach%20to%20skin%20care.pdf, Retrieved Sep. 26, 2013.

Deschaume et al., "Interactions of aluminum hydrolytic species with biomolecules," New Journal of Chemistry, 2008, 32:1346-1353.

European Food Safety Authority, "Scientific Opinion on the safety and efficacy tetra-basic zinc chloride for all animal species," EFSA Journal, 2012, 10(5):2672.

Hartwell et al., "Preparation and characterization of tyrosine and lysine metal chelate polyesters and polyamides", J. of the American Chem. Society, Mar. 1970, 92(5):1284-1289.

(Continued)

*Primary Examiner* — Anoop K Singh
*Assistant Examiner* — Doan T Phan

(57) ABSTRACT

A personal care composition for application to the skin or hair comprising a cosmetically acceptable carrier and zinc X halide precursors wherein the precursors are a zinc ion source, an X source, and a halide source, wherein the halide source can be part of the zinc ion source, the X source, or a halogen acid, wherein the precursors can complex into the zinc X halide when the composition is applied to the skin or hair, wherein X is an amino acid or trimethylglycine. Methods of making and using the compositions are also provided. When the precursors complex into a zinc X halide, the complex can be used to deliver zinc salts to block perspiration and provide antibacterial effects.

15 Claims, No Drawings

(56) References Cited

U.S. PATENT DOCUMENTS

| | | | |
|---|---|---|---|
| 4,599,152 A | 7/1986 | Ashmead | |
| 4,684,528 A | 8/1987 | Godfrey | |
| 4,687,663 A | 8/1987 | Schaeffer | |
| 4,842,847 A | 6/1989 | Amjad | |
| 4,866,161 A | 9/1989 | Sikes et al. | |
| 4,885,155 A | 12/1989 | Parran, Jr. et al. | |
| 5,004,597 A | 4/1991 | Majeti et al. | |
| 5,061,815 A * | 10/1991 | Leu | A23L 1/3045 426/74 |
| 5,156,845 A | 10/1992 | Grodberg | |
| 5,188,821 A | 2/1993 | Gaffar et al. | |
| 5,192,531 A | 3/1993 | Gaffar et al. | |
| 5,504,055 A | 4/1996 | Hsu | |
| 5,643,559 A | 7/1997 | Eigen et al. | |
| 5,698,724 A | 12/1997 | Anderson et al. | |
| 5,707,679 A | 1/1998 | Nelson | |
| 5,714,447 A * | 2/1998 | Jones | A61K 8/27 510/130 |
| 5,911,978 A | 6/1999 | Carr et al. | |
| 5,993,784 A | 11/1999 | Hill | |
| 6,121,315 A | 9/2000 | Nair et al. | |
| 6,156,293 A | 12/2000 | Jutila et al. | |
| 6,607,711 B2 | 8/2003 | Pedersen | |
| 6,649,153 B1 | 11/2003 | Parekh et al. | |
| 6,685,920 B2 | 2/2004 | Baig et al. | |
| 6,969,510 B2 | 11/2005 | Holerca et al. | |
| 8,067,627 B2 | 11/2011 | Newsome et al. | |
| 8,247,398 B2 | 8/2012 | Goel | |
| 2003/0077332 A1 * | 4/2003 | Godfrey | A61K 31/198 424/642 |
| 2004/0042978 A1 | 3/2004 | Embro | |
| 2004/0122088 A1 | 6/2004 | Newsome et al. | |
| 2004/0033916 A1 | 10/2004 | Holerca et al. | |
| 2004/0198998 A1 | 10/2004 | Holerca et al. | |
| 2006/0024252 A1 | 2/2006 | Esposito et al. | |
| 2006/0024381 A1 * | 2/2006 | Schwartz | A61K 8/27 424/641 |
| 2007/0071698 A1 | 3/2007 | Doss | |
| 2009/0220444 A1 | 9/2009 | Teckenbrock et al. | |
| 2010/0021573 A1 | 1/2010 | Gonzalez et al. | |
| 2010/0266480 A1 | 10/2010 | Huang | |
| 2010/0330163 A1 | 12/2010 | Soparkar | |
| 2011/0076309 A1 | 3/2011 | Misner et al. | |
| 2011/0229536 A1 | 9/2011 | Kvitnitsky et al. | |
| 2013/0017240 A1 | 1/2013 | Porter et al. | |
| 2014/0170086 A1 | 6/2014 | Pan et al. | |

FOREIGN PATENT DOCUMENTS

| | | |
|---|---|---|
| CN | 102811698 | 12/2012 |
| CN | 103156073 | 6/2013 |
| CN | 103535536 | 1/2014 |
| DE | 735096 | 5/1943 |
| EP | 0083486 | 12/1982 |
| EP | 0108937 | 5/1984 |
| EP | 0508524 | 10/1992 |
| EP | 0514553 | 11/1992 |
| EP | 0842664 | 5/1998 |
| EP | 1021158 | 7/2000 |
| EP | 1064946 | 1/2001 |
| EP | 1203575 | 5/2002 |
| EP | 1319394 | 6/2003 |
| EP | 1935395 | 6/2008 |
| EP | 1529775 | 5/2011 |
| FR | 2241301 | 3/1975 |
| GB | 2052978 | 2/1981 |
| GB | 2109685 | 6/1983 |
| GB | 2243775 | 11/1991 |
| JP | S57-158724 | 9/1982 |
| JP | 2004175790 | 6/2004 |
| JP | 2009084201 | 4/2009 |
| JP | 2010132639 | 6/2010 |
| WO | WO86/00004 | 1/1986 |
| WO | WO9917735 | 4/1999 |
| WO | WO199917735 | 4/1999 |
| WO | WO0169087 | 9/2001 |
| WO | WO2004054531 | 7/2004 |
| WO | WO2004/064536 | 8/2004 |
| WO | WO2007063507 | 6/2007 |
| WO | WO2011053291 | 5/2011 |
| WO | WO2011/088199 | 7/2011 |
| WO | WO2011/123123 | 10/2011 |
| WO | WO2014/098813 | 6/2014 |
| WO | WO2014/098814 | 6/2014 |
| WO | WO2014/098818 | 6/2014 |
| WO | WO2014/098819 | 6/2014 |
| WO | WO2014/098821 | 6/2014 |
| WO | WO2014/098822 | 6/2014 |
| WO | WO2014/098824 | 6/2014 |
| WO | WO2014/099164 | 6/2014 |
| WO | WO2014/099165 | 6/2014 |
| WO | WO2014/099166 | 6/2014 |
| WO | WO2014/099167 | 6/2014 |
| WO | WO2014098825 | 6/2014 |
| WO | WO2014098826 | 6/2014 |
| WO | WO2014098828 | 6/2014 |
| WO | WO2014098829 | 6/2014 |
| WO | WO2014099039 | 6/2014 |
| WO | WO2014099226 | 6/2014 |
| WO | WO2014204439 | 12/2014 |

OTHER PUBLICATIONS

International Search Report and Written Opinion for International Application No. PCT/US2012/070489 dated Oct. 22, 2013.
International Search Report and Written Opinion for International Application No. PCT/US2012/070492 dated Oct. 22, 2013.
International Search Report and Written Opinion for International Application No. PCT/US2012/070498 dated Sep. 4, 2013.
International Search Report and Written Opinion for International Application No. PCT/US2012/070501 dated Oct. 21, 2013.
International Search Report and Written Opinion for International Application No. PCT/US2012/070505 dated Nov. 20, 2013.
International Search Report and Written Opinion for International Application No. PCT/US2012/070506 dated Oct. 14, 2013.
International Search Report and Written Opinion for International Application No. PCT/US2012/070513 dated Oct. 14, 2013.
International Search Report and Written Opinion for International Application No. PCT/US2012/070521 dated Sep. 30, 2013.
International Search Report and Written Opinion for International Application No. PCT/US2012/070525 dated Sep. 27, 2013.
International Search Report and Written Opinion for International Application No. PCT/US2012/070528 dated Sep. 30, 2013.
International Search Report and Written Opinion for International Application No. PCT/US2012/070534 dated Sep. 26, 2013.
International Search Report and Written Opinion for International Application No. PCT/US2012/070537 dated Oct. 11, 2013.
International Search Report and Written Opinion for International Application No. PCT/US2013/046268 dated Apr. 22, 2014.
International Search Report and Written Opinion for International Application No. PCT/US2013/050845 dated Aug. 13, 2014.
International Search Report and Written Opinion for International Application No. PCT/US2013/068852 dated Nov. 10, 2014.
International Search Report and Written Opinion for International Application No. PCT/US2013/068854 dated Oct. 20, 2014.
International Search Report and Written Opinion for International Application No. PCT/US2013/068859 dated Aug. 4, 2014.
International Search Report and Written Opinion for International Application No. PCT/US2013/068860 dated Oct. 22, 2014.
International Search Report and Written Opinion for International Application No. PCT/US2013/070932 dated Jul. 24, 2014.
International Search Report and Written Opinion for International Application No. PCT/US2014/042947 dated Aug. 22, 2014.
International Search Report and Written Opinion for International Application No. PCT/US2014/042948 dated Aug. 26, 2014.
International Search Report and Written Opinion for International Application No. PCT/US2014/043051 dated Feb. 18, 2015.
Kondrot, "The Importance of Zinc," http://www.healingtheeye.com/Articles/zinc.html, Feb. 21, 2012.

(56) References Cited

OTHER PUBLICATIONS

Liang et al., "In vitro scratch assay: a convenient and inexpensive method for analysis of cell migration in vitro," Nature Protocols, 2007, 2(2):329-333.
Liu et al., "The research on zinc coordination number 5 odd structure in zinc complex with L-lysine," J. Molecular Science, 2000, 16(2):114-117, abstract only in English.
Lu et al., "Albumin as a zinc carrier: properties or its high-affinity zinc-binding site". Biochem. Soc. Trans., 2008, 36:1317-1321.
Lynch, "Zinc in the mouth, its interactions with dental enamel and possible effects on caries: a review of the literature," Int. Dent. J., Aug. 2011, Suppl 3:46-54.
Mavromichalis et al., "Growth-promoting efficacy of pharmacological doses of tetrabasic zinc chloride in diets for nursery pigs," Canadian Journal of Animal Science, pp. 387-391, Jan. 2001.
McAuliffe et al., "Metal complexes of sulphur-containing amino acids," Inorganica Chimica Acta Reviews, Dec. 1972, 6:103-121.
Moore et al., "Antibacterial activity of gutta-percha cones attributed to the zinc oxide component," Oral Surgery, 1982, 53:508-517.
Mosmann, "Rapid colorimetric assay for cellular growth and survival: Application to proliferation and cytotoxicity assays," J. Immunol. Methods, 1983, 65:55-63.
Pashley et al. Dentin permeability effects of desensitizing dentifrices in vitro. J Periodontol. 1984:55(9):522-525.
Prasad, "Zinc:role in immunity, oxidative stress and chronic inflammation," Current Opinion in Clinical Nutrition and Metabolic Care, 2009, 12:646-652.
Rigano, L., Zinc Lauryl Ether Sulphate—A New Approach to Skin Care, SOFW Journal, Apr. 2004, 128:26-33.
Schmetzer et al., "Wulfingite, $\epsilon$-Zn(OH)2, and simonkolleite, ZnS(OH)8C12•H2O, two new minerals from Richelsdorf, Hesse, F.R.G.," N. Jb. Miner. Mh., Apr. 1985, pp. 145-154.
Seil et al. "Antibacterial effect of zinc oxide nanoparticles combined with ultrasound," Nanotechology,2012, 23:495101.
Soderling et al., "Betaine-containing toothpaste relieves subjective symptoms of dry mouth," Acta Odontol. Scand., Apr. 1998, 56(2):65-9.
Stewart et al., "Interdomain zinc site on human albumin," PNAS, 2003, 100(7):3701-3706.
Tian et al., "Using DGGE profiling to develop a novel culture medium suitable for oral microbial communities," Molecular Oral Microbiology, 2010, 25(5):357-367.
Twetman et al., 2003, "Caries-preventative effect of fluoride toothpaste a systematic review," Acta Odontol Scand., Dec. 2003, 61(6):347-55.
Wachi et al., "Antibacterial compsn. Zinc oxide—solubilized by amino acid, amino acid hydrochloride and/or amino acid alkali metal salt," Sep. 1982, vol. 1982(45).
Wallhausser et al., "Antimicrobial Preservatives in Europe: Experience with preservatives used in pharmaceuticals and cosmetics," Develop. Biol. Standard, 1974, 24:9-28.
Yao et al., "An investigation of zirconium(IV)-glycine(CP-2) hybrid complex in bovine serum albumin protein matrix under varying conditions," J. of Materials Chemistry, 2011, 21:19005-19012.
Yousef et al., "In vitro antibacterial activity and minimum inhibitory concentration of zinc oxide and nano-particle zinc oxide against pathogenic strains," J. of Health Sciences, 2012, 2(4):38-42.
Zhu et al., "Synthesis and Crystal Structure of [Zn+{H2N(CH2)4CH(NH2)COONa}2SO4-] •H20," Chinese Science Bulletin, Sep. 1990, 35(18):1521-1525.

* cited by examiner

COMPOSITION WITH ZINC AMINO ACID/TRIMETHYLGLYCINE HALIDE PRECURSORS

CROSS-REFERENCE TO RELATED APPLICATIONS

This application is a United States National Stage Application under 35 U.S.C. § 371 of International Application PCT/US2012/070492, filed on Dec. 19, 2012, the contents of which is hereby incorporated by reference in its entirety.

BACKGROUND OF THE INVENTION

Antiperspirants based on aluminum or aluminum/zirconium salts are known. These materials function as antiperspirants by plugging pores thereby blocking sweat release. Antiperspirant compositions containing aluminum or aluminum-zirconium salts tend to exhibit polymerization of these salts over time, forming species with molecular weights ranging from about 500 to about 500,000 g/mol. In general, lower molecular weight species have greater antiperspirant effect than higher molecular weight species. Without being bound by theory, it is believed that the smaller molecules more readily and more effectively occlude sweat pores, thereby producing the desired antiperspirant effect. Maintaining a relatively low molecular weight and avoiding excessive polymerization enhances the antiperspirant effect and moreover lowers the amount of antiperspirant salt which necessary to control perspiration.

Underarm deodorants control odor by eliminating the bacteria that cause odor. Conventional antiperspirant salts tend to be acidic in aqueous solution, a property which makes them effective bacteriocides, thereby providing a deodorant benefit, but which can also cause skin irritation.

There is a need for additional antiperspirant active agents that provide molecular weight complexes of a size capable of plugging pores to block sweat, that provide deodorant/antibacterial efficacy, and that are less irritating to the skin than the acidic salts in conventional antiperspirants.

BRIEF SUMMARY OF THE INVENTION

The invention provides a personal care composition, for example an antiperspirant or deodorant composition, which delivers to the skin a zinc X halide, i.e., a complex of zinc ion, an X residue, and halide ion, such as zinc lysine chloride ($ZnLysine_2Cl_2$ or $ZnLysine_3Cl_2$), for example, wherein X refers to amino acid or trimethylglycine. In one embodiment, the invention provides a composition comprising zinc X halide and/or zinc X halide precursor materials which form a zinc X halide in situ (for example zinc ion source plus an amino acid hydrohalide, or zinc halide plus an amino acid or trimethylglycine, or zinc ion source plus halogen acid plus amino acid or trimethylglycine). The zinc ion source to produce the zinc X halide is a material that can release $Zn^{2+}$ in aqueous solution in the presence of an amino acid or trimethylglycine, for example zinc oxide or tetrabasic zinc chloride. As the zinc X halide provides antibacterial properties, the invention also encompasses other personal care compositions for application to the skin, for example hand soaps or body washes, comprising a zinc X halide and/or precursors thereof. The invention further provides methods of reducing sweat comprising applying the composition to skin, and methods of killing bacteria comprising contacting the bacteria with the composition. Trimethylglycine as used throughout refers to N,N,N-trimethylglycine.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The invention therefore provides, in a first embodiment, personal care composition for application to the skin or hair comprising a cosmetically acceptable carrier and zinc X halide precursors wherein the precursors are a zinc ion source, an X source, and a halide source, wherein the halide source can be part of the zinc ion source, the X source, or a halogen acid, wherein the precursors can complex into the zinc X halide when the composition is applied to the skin or hair. (Composition 1), e.g., 1.1. Any of the foregoing compositions wherein the zinc ion source is at least one of zinc oxide, zinc chloride, tetrabasic zinc chloride, zinc carbonate, zinc nitrate, zinc citrate, and zinc phosphate.

1.2. Any of the foregoing compositions wherein the amino acid source is at least one of a basic amino acid, lysine, arginine, and glycine.

1.3. Any of the foregoing compositions wherein the precursors are zinc oxide and an amino acid hydrohalide.

1.4. Any of the foregoing compositions wherein the precursors are tetrabasic zinc chloride and at least one of an amino acid, an amino acid hydrohalide, or trimethylglycine, optionally the zinc X halide is made by combining TBZC with lysine, lysine hydrochloride, or trimethylglycine.

1.5. Any of the foregoing compositions wherein the zinc X halide is formed, in whole or in part, in situ after the composition is formulated.

1.6. Any of the foregoing compositions wherein the zinc X halide formed from the precursors has the formula $ZnLysine_2Cl_2$ or $ZnLysine_3Cl_2$, wherein Zn is divalent zinc ion, X is amino acid or trimethylglycine residue, and Hal is halide ion.

1.7. Any of the foregoing compositions, wherein the amino acid is lysine.

1.8. Any of the foregoing compositions, wherein the zinc X halide is present in an amount of 0.05 to 40% by weight of the composition, optionally at least 0.1, at least 0.2, at least 0.3, at least 0.4, at least 0.5, at least 1, at least 2, at least 3, or at least 4 up to 40% by weight of the composition, or, optionally, 0.1 up to 30%, up to 20%, up to 10%, up to 5%, up to 4%, up to 3%, up to 2%, or up to 1% by weight of the composition.

1.9. Any of the foregoing compositions, wherein the X source is present in an amount of 0.05 to 30% by weight of the composition, optionally at least 0.1, at least 0.2, at least 0.3, at least 0.4, at least 0.5, at least 1, at least 2, at least 3, at least 4, at least 5, at least 10, at least 15, at least 20 up to 30% by weight.

1.10. Any of the foregoing compositions, wherein zinc oxide and amino acid hydrohalide are present in amounts such that if combined into the zinc X halide, the zinc X halide would be present in an amount of 0.05 to 40% by weight of the composition, optionally at least 0.1, at least 0.2, at least 0.3, at least 0.4, at least 0.5, at least 1, at least 2, at least 3, or at least 4 up to 40% by weight of the composition, or, optionally, 0.1 up to 30%, up to 20%, up to 10%, up to 5%, up to 4%, up to 3%, up to 2%, or up to 1% by weight of the composition.

1.11. Any of the foregoing compositions, wherein a molar ratio of zinc to amino acid or trimethylglycine is 2:1 to 1:4, optionally 1:1 to 1:4, 1:2 to 1:4, 1:3 to 1:4, 2:1 to 1:3, 2:1 to 1:2, 2:1 to 1:1, or 1:3

1.12. Any of the foregoing compositions, wherein a total amount of zinc present in the composition is 0.05 to 10% by weight.

1.13. Any of the foregoing compositions, wherein the halide is selected from the group consisting of chloride, bromide, and iodide.

1.14. Any of the foregoing compositions, wherein the zinc X halide formed from the precursors is zinc lysine chloride.

1.15. Any of the foregoing compositions, in an anhydrous carrier.

1.16. Any of the foregoing compositions, which is anhydrous composition comprising zinc oxide and amino acid hydrohalide.

1.17. Any of the foregoing compositions wherein the halide is chloride.

1.18. Any of the foregoing compositions wherein the amino acid is lysine.

1.19. Any of the foregoing compositions wherein the zinc X halide formed from the precursors is zinc lysine chloride (ZnLysine$_2$Cl$_2$ or ZnLysine$_3$Cl$_2$).

1.20. Any of the foregoing compositions in a cosmetically acceptable base suitable for application to the skin, e.g., a cosmetically acceptable base comprising one or more of water-soluble alcohols (such as C$_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

1.21. The foregoing composition wherein the cosmetically acceptable base is anhydrous, e.g., comprises less than 5% water.

1.22. Any of the foregoing compositions, wherein the composition is an antiperspirant and/or deodorant, e.g., an antiperspirant stick, an aerosol antiperspirant spray, or a liquid roll-on antiperspirant.

1.23. Any of the foregoing compositions 1-20, wherein the composition is a body wash, a shower gel, a bar soap, a shampoo, or hair conditioner.

The invention further provides methods of reducing perspiration comprising applying an antiperspirant effective amount of any of Composition 1, et seq. to the skin, methods of reducing body odor comprising applying a deodorant-effective amount of any of Composition 1, et seq. to the skin, and methods of killing bacteria comprising contacting the bacteria with an antibacterially effective amount of a composition, e.g., any of Composition 1, et seq.

The invention further provides a method of making a composition comprising combining zinc X halide precursors wherein the precursors are a zinc ion source, an X source, and a halide source, wherein the halide source can be part of the zinc ion source, the X source, or a halogen acid in a cosmetically acceptable base material.

The invention further provides a method of forming a zinc X halide comprising applying a composition, e.g., any of Composition 1, et seq. to skin or hair.

The invention further provides (i) the use of zinc precursors to form a zinc X halide to kill bacteria, reduce perspiration, and/or reduce body odor, wherein the precursors are a zinc ion source, an X source, and a halide source, wherein the halide source can be part of the zinc ion source, the X source, or a halogen acid.

Without intending to be bound by theory, it is believed that the formation of the zinc X halide proceeds via formation of the zinc halide then coordination of amino acid residues around a central zinc. Using reaction of zinc oxide with lysine hydrochloride in water as an example, ZnO reacts with lysine.HCl via dissociation of the hydrochloride to allow the reaction: ZnO+HCl→?ZnCl$_2$+H$_2$O. One mole of ZnCl$_2$ will react with 3 moles of lysine to form a clear solution of Zn-lysine-chloride complex (ZnLysine$_2$Cl$_2$ or ZnLysine$_3$Cl$_2$), believed to have the structure depicted in Formula 1, wherein R denotes the amino acid side chain:

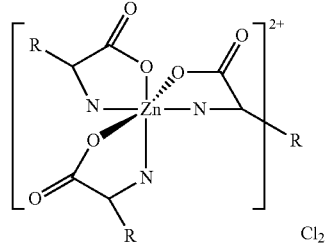

Formula 1

In this configuration, Zn is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry. This appears to be the dominant complex. Other complexes of zinc and lysine are possible, e.g., if there is insufficient halide, e.g., ZnOLys$_2$, having a pyramid geometry, with the equatorial plane that is same as the above compound (Zn is bound to two oxygen and two nitrogen atoms from different lysines), wherein the top of the pyramid is occupied by an O atom. More complex structures involving multiple zinc ions are also possible, based on the TBZC structure. The zinc can also have the zinc structure present in zinc stearate.

The interaction of zinc and amino acid or trimethylglycine converts the insoluble ZnO or TBZC to a highly soluble complex at approximately neutral pH. In the sweat duct, which contains charged molecules such as proteins and fatty acids, the complex will flocculate forming a precipitate that blocks the sweat ducts. To the extent the complex is disrupted in these conditions, releasing free zinc ion, the zinc ion can hydrolyze to form amorphous zinc hydroxide precipitate, further blocking the ducts, and moreover, the zinc ion can kill underarm bacteria, thereby reducing underarm odor. One advantage over conventional aluminum or aluminum/zirconium antiperspirant salts is that the complex is forms near neutral pH, whereas the conventional antiperspirant salts are acidic, which can cause irritation to the skin.

It will be understood that other amino acids can be used in place of lysine in the foregoing scheme. It will also be understood that, although the zinc, amino acid or trimethylglycine and halide may be primarily in the form of precursor materials or in the form of a complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

Zinc X halide precursors, for example the ZnO and lysine hydrochloride in the foregoing example, can be incorporated into a suitable base, for example an anhydrous stick or aerosol. Upon sweating, the soluble zinc X halide complex is formed, which can reduce sweat and odor as described above. Alternatively, the soluble complex can be incorporated in a product having an aqueous base, such as a roll-on or spray, to reduce sweat and odor.

As used herein, the term antiperspirant can refer to any material that can form a plug in a pore to reduce sweating, or antiperspirant refers to those materials classified as antiperspirants by the Food and Drug Administration under 21 CFR part 350. Antiperspirants may also be deodorants, particularly in the case of this invention, as the zinc X halide has antibacterial properties and can reduce odor-causing bacteria on the skin.

Precursors, which can react in situ with water to form the zinc X halide. In one embodiment, the zinc X halide can be prepared at room temperature by mixing the precursors in a solution, such as water. The in situ formation provides ease of formulation. The precursors can be used instead of first having to form the zinc X halide. In another embodiment, the water permitting formation of the zinc X halide from the precursor comes from sweat that comes into contact with the composition after application.

The combination of the zinc, the X, and the halide forms a cationic complex-halide salt. The zinc X halide is a water soluble complex formed from the halide acid addition salt of zinc (e.g., zinc chloride) and an amino acid, or from the halide acid addition salt of an amino acid (e.g., lysine hydrochloride) and zinc ion source, e.g., zinc oxide or TBZC, and/or from combination of all three of a halogen acid, an amino acid, and a zinc ion source.

The zinc ion source for combination with an amino acid hydrohalide or an X plus halogen acid may be any source that provides $Zn^2$ ions efficiently, for example zinc oxide, zinc chloride, tetrabasic zinc chloride, zinc carbonate, zinc nitrate, zinc citrate, and zinc phosphate. Zinc oxide is a white powder, insoluble in water. Tetrabasic zinc chloride (TBZC) or zinc chloride hydroxide monohydrate is a zinc hydroxy compound with the formula $Zn_5(OH)_8Cl_2 \cdot H_2O$, also referred to as basic zinc chloride, zinc hydroxychloride, or zinc oxychloride. It is a colorless crystalline solid insoluble in water. Both of these materials are found to be soluble in water in the presence of an amino acid and provide a source of zinc ions while restricting the available anions, as an excess of anions can interfere with the complex formation.

The amino acid source can be any amino acid. Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid.

In some embodiments, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine. In other embodiments, the amino acid is arginine. Neutral amino acids, such as glycine, and even acidic amino acids, such as aspartic acid, however, are also capable of forming salts with strong acids, such as halogen acids. In some embodiments the amino acid is a neutral or acidic amino acid, e.g., glycine.

The halide source can be part of the zinc source, such as zinc chloride or tetrabasic zinc chloride. The halide source can be part of the amino acid, such as an amino acid hydrohalide. Also, the halide source can be a halogen acid. The halide may be chlorine, bromine, or iodine, most typically chlorine. The acid addition salt of an amino acid and a halogen acid (e.g., HCl, HBr, or HI) is sometimes referred to herein as an amino acid hydrohalide. Thus one example of an amino acid hydrohalide is lysine hydrochloride.

In certain embodiments, the amount of zinc X halide in the composition is 0.05 to 10% by weight of the composition. In certain embodiments, precursors, e.g., zinc oxide and amino acid hydrohalide, are present in amounts such that when combined into the zinc X halide, the zinc X halide would be present in an amount of 0.05 to 10% by weight of the composition. In either of these embodiments, the amount of the zinc X halide can be varied for the desired purpose, such as an antibacterial agent or as an antiperspirant. In other embodiments, the amount of the zinc X halide is at least 0.1, at least 0.2, at least 0.3, at least 0.4, at least 0.5, at least 1, at least 2, at least 3, or at least 4 up to 10% by weight of the composition. In other embodiments, the amount of the zinc X halide is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, zinc ion source, such as zinc oxide or TBZC, is present in an amount of 0.05 to 10% by weight of the composition. In other embodiments, the amount of zinc ion source is at least 0.1, at least 0.2, at least 0.3, at least 0.4, at least 0.5, at least 1, at least 2, at least 3, or at least 4 up to 10% by weight of the composition. In other embodiments, the amount of the zinc oxide or TBZC is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, X source is present in an amount of 0.05 to 30% by weight. In other embodiments, the amount is at least 0.1, at least 0.2, at least 0.3, at least 0.4, at least 0.5, at least 1, at least 2, at least 3, at least 4, at least 5, at least 10, at least 15, at least 20 up to 30% by weight. In other embodiments, the amount is less than 30, less than 25, less than 20, less than 15, less than 10, less than 5, less than 4, less than 3, less than 2, or less than 1 down to 0.05% by weight of the composition.

Where precursor materials are present, they are preferably present in molar ratios approximately as required to produce the desired zinc X halide, although an excess of one material or another may be desirable in certain formulations, e.g., to balance pH against other formulation constituents, to provide additional antibacterial zinc, or to provide X buffer. Preferably, however, the amount of halide is limited, as constraining the level of halide somewhat encourages interaction between the zinc and the X. For example, in one embodiment to produce zinc lysine chloride ($ZnLysine_2Cl_2$ or $ZnLysine_3Cl_2$), the molar ratios of the elements in the precursor materials would include about 1 molar equivalent $Zn^2$:3 molar equivalents Lys:2 molar equivalents $Cl^-$.

In some embodiments, the total amount of zinc in the composition is 0.05 to 10% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

In certain embodiments, a molar ratio of zinc to X is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., zinc oxide or TBZC and X, will not significantly react to form the zinc X halide. When contacted with a sufficient amount of water, which can be in the form of sweat, the precursors will then react to form the zinc X halide. The zinc X halide when introduced into a sweat duct will flocculate with protein and/or hydrolyze with water and/or sweat to form a precipitate to block the sweat duct.

In certain embodiments, the zinc X halide can have a conductivity of greater than 8000, optionally greater than 9000, greater than 10,000, or greater than 12,000 µS/cm preferably when the pH is at least 4.

The composition can be any type of composition. In certain embodiments, the composition is any composition in which it is desired to include an antibacterial agent for application to the skin. Examples of such compositions include, but are not limited to, personal care compositions, antiperspirants, deodorants, body washes, shower gels, bar soaps, shampoo, hair conditioners, cosmetics.

The carrier represents all other materials in the composition other than the zinc X halide or the zinc salt and X. The amount of carrier is then the amount to reach 100% by adding to the weight of the zinc X halide or the zinc salt and X.

For antiperspirant/deodorant compositions, the carrier can be any carrier that is used for antiperspirants/deodorants. The carrier can be in the form of a stick, a gel, a roll-on, or an aerosol. For stick formulations, the carrier may include oils and/or silicones and gelling agents. An example of a formulation can be found in US2011/0076309A1, incorporated by reference herein.

Optional ingredients that can be included in an antiperspirant and/or deodorant formulation of the compositions of the invention include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments. If desired, an antiperspirant and/or deodorant agent additional to the zinc X halide can be included, for example an odor reducing agent such as a sulfur precipitating agent, e.g., copper gluconate, zinc gluconate, zinc citrate, etc.

The antiperspirant compositions can be formulated into topical antiperspirant and/or deodorant formulations suitable for application to skin, illustratively a stick, a gel, a cream, a roll-on, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. The antiperspirant and/or deodorant formulation can be provided in any suitable container such as an aerosol can, tube or container with a porous cap, roll-on container, bottle, container with an open end, etc.

The compositions can be used in a method to reduce sweating by applying the composition to skin. In certain embodiments, the application is to axilla. Also, the compositions can be used to kill bacteria by contacting bacteria with the composition. For example, in one embodiment, the combination of the amino acid or amino acid hydrohalide with the zinc oxide increases the availability of zinc ions, which can then kill bacteria and reduce sweat.

Thus the invention provides (i) a method for controlling perspiration comprising applying to skin an antiperspirant effective amount of a formulation of any embodiment embraced or specifically described herein, e.g., any of Compositions 1 et seq.; and (ii) a method for controlling odor from perspiration comprises applying to skin a deodorant effective amount of a formulation of any embodiment embraced or specifically described herein, e.g., any of Compositions 1 et seq.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

Example 1—Solubilization of Zinc by Amino Acid

Zn concentration of TBZC is compared with ZnO and TBZC with amino acids. Ingredients are dispersed in water, equilibrated overnight, and the supernatant analyzed for free $Zn^{2+}$ by atomic absorption. Table 1 shows comparison of free Zn concentration of TBZC with ZnO and TBZC mixed with different amino acids.

TABLE 1

|  | Free Zn (ppm) |
|---|---|
| TBZC + Arginine (4 + 4%) | 1819 |
| TBZC + Lysine-HCl (4 + 4%) | 6000 |
| TBZC + Lysine (4 + 4%) | 5000 |
| TBZC (4%) | 64.8 |
| ZnO(4%) | 11 |
| ZnO + Lysine-HCl (4 + 4%) | 21700 |

Free zinc ion concentration provided by TBZC is somewhat higher than with ZnO. This shows that while both have low solubility, the solubility of TBZC is somewhat better than ZnO. The free Zn concentration is dramatically increased when amino acid is added. For example, solubility increases 28 times when arginine is added and near 100 times when lysine hydrochloride is mixed with TBZC. Lysine hydrochloride also greatly enhances the solubility of zinc oxide.

Example 2—Antibacterial Effects

A zone of inhibition test is conducted on several materials: zinc oxide and amino acid hydrohalide alone and a mixture formed from zinc oxide and amino acid hydrohalide. The method involves making a lawn of freshly prepared bacterial culture on TSA (trypticase soy agar) plates. Sterile filter paper discs are seeded with 20 μl of test sample (supernatant or mixture). Sample-coated filter paper discs are air dried and applied onto the bacterial lawn on TSA plates. Plates are incubated for 20 hours at 37° C. The results are shown below in Table 2.

TABLE 2

| Material | Sample | Zone of Inhibition (mm) Wet Sample | | | Zone of Inhibition (mm) Dry Sample | | |
|---|---|---|---|---|---|---|---|
|  |  | S. aureus | S. epider. | C. xerosis | S. aureus | S. epider. | C. xerosis |
| ZnO 4% | Supernatant | 0 | 0 | 0 | 0 | 0 | 0 |
|  | Mixture | 7 | 12 | 0 | 7 | 10 | 0 |
| Lysine-HCl 23.2% | As is | 0 | 0 | 0 | 0 | 0 | 0 |
| ZnO 4% + lysine HCl 23.2% | Supernatant | 12 | 23 | 18 | 13 | 22 | 17 |
|  | Mixture | 14 | 25 | 19 | 14 | 24 | 18 |

As can be seen from the table, when the zinc amino acid halide is formed, the compositions increase in antibacterial activity compared to zinc oxide alone or amino acid hydrohalide alone.

Similar antibacterial efficacy is seen when tetrabasic zinc chloride is used in place of zinc oxide as the source of zinc ions. Results are in Table 3 below.

TABLE 3

| Sample | | Zone of Inhibition (mm) | |
|---|---|---|---|
|  |  | S. aureus | C. minutissimum |
| Arginine 4% |  | 0 | 0 |
| Lysine 4% |  | 0 | 0 |
| Lysine HCl 4% |  | 0 | 0 |
| TBZC 4% | Supernat | 6 | 7 |
|  | Mixture | 6 | 7 |
| TBZC 4% + arginine 4% | Supernat | 8 | 12 |
|  | Mixture | 7.5 | 16 |
| TBZC 4% + lysine 4% | Supernat | 7 | 21 |
|  | Mixture | 9 | 16 |
| TBZC 4% + lysine HCl 4% | Supernat | 9 | 20 |
|  | Mixture | 7 | 17 |

As can be seen from the table, when the zinc amino acid halide is formed, the compositions increase in antibacterial activity compared to tetrabasic zinc chloride alone or amino acid alone.

Example 3: Mechanisms of Sweat Reduction

A zinc lysine hydrochloride (ZLC) is prepared by mixing ZnO+2(Lysine.HCl) in the presence of water to yield [Zn(Lysine)$_2$Cl]$^+$Cl$^-$.2H$_2$O.

Hydrolysis Reaction:

A 185 mg/ml solution of ZLC is prepared and diluted several-fold and aged in a 37° C. oven over 5 hours for turbidity studies. A white precipitate forms as the solution is diluted. Turbidity of the solutions is measured using a nephelometer, results being given in nephelometric turbidity units (NTU). Table 4 shows a comparison of pH and turbidity before and after aging, showing an increase in turbidity with dilution and with aging:

TABLE 4

|  | 185 mg/ml | 92.5 mg/ml | 46.25 mg/ml | 23.125 mg/ml | 11.56 mg/ml | 5.78 mg/ml |
|---|---|---|---|---|---|---|
| initial pH | 6.8 | 7 | 7.4 | 7.7 | 7.8 | 8 |
| initial turbidity (NTU) | 4.7 | 2.8 | 1.5 | 0.7 | 14.8 | 40.1 |
| pH after aging | 6.8 | 7 | 7.4 | 7.7 | 7.8 | 8 |

TABLE 4-continued

|  | 185 mg/ml | 92.5 mg/ml | 46.25 mg/ml | 23.125 mg/ml | 11.56 mg/ml | 5.78 mg/ml |
|---|---|---|---|---|---|---|
| turbidity after aging (NTU) | 4.1 | 2.6 | 2.8 | 247.4 | >1000 | >1000 |

The precipitates formed in the 8×, 16× and 32× diluted solutions are collected by centrifugation and identified as crystalline ZnO by PXRD. From the supernatant, a single crystal is grown and shown by X-ray diffraction to be Lysine Monohydrochloride Dihydrate (Lysine.HCl.2H$_2$O). These data indicate that the ZLC complex disassociates upon dilution, with consequent precipitation of zinc oxide.

The mechanism of the ZLC hydrolysis reaction can be expressed as

[Zn(Lysine)$_2$Cl]$^+$Cl$^-$.2H$_2$O+H$_2$O→ZnO+ Lysine.HCl.2H$_2$O

In an underarm product, a mixture of ZnO+lysine HCl, in the presence of sweat, will form ZLC, which will enter the sweat duct and form a plug of ZnO.

Flocculation:

Another mechanism by which the ZLC blocks sweat release involves flocculation of ZLC in the presence of protein. Bovine Serum Albumin (BSA) is used as the protein in this study. Control solution (DI water) and three 1% BSA aqueous solutions with different pH are prepared as set forth on Table 5:

TABLE 5

|  | sample 1 | sample 2 | sample 3 |
|---|---|---|---|
| H$_2$O | 15 ml | 15 ml | 15 ml |
| BSA | 0 g | 155.1 mg | 155.2 mg |
| % BSA w/w | 0% | 1% | 1% |
| pH | 6.4 | 7.2 | adjusted to 5.1 |
| Turbidity(NTU) | 0.35 | 3.6 | 10.6 |
| Observation | Transparent | Transparent | Transparent |

ZLC powder is added to the above samples to study the interaction between ZLC and BSA and to determine whether ZLC has astringent properties, i.e., whether it can form a precipitate and thus behave as an antiperspirant. Turbidity and pH of solutions are measured 5 hours after the mixtures were placed in a 37° C. oven, and the results are shown in Table 6.

TABLE 6

|  | sample 1 | sample 2 | sample 3 |
|---|---|---|---|
| ZLC added | 151.1 mg | 151.1 mg | 150.9 mg |
| ZLC concentration in solution | about 0.98% w/w or 15 mg/ml | about 0.96% w/w or 15 mg/ml | about 0.96% w/w or 15 mg/ml |
| observation | transparent solution becomes slightly cloudy | a lot white precipitate formed, solution becomes very cloudy | a lot white precipitate formed, solution becomes very cloudy |
| pH | 8 | 8.2 | 8 |
| Turbidity (NTU) | 357 | >1000 | >1000 |

Thus, in the sweat duct (pH=5-7), ZLC will hydrolyze to insoluble ZnO to physically block the sweat ducts. In addition, ZLC also has the ability to flocculate proteins, such as BSA, in the sweat, thus enhancing the formation of "plugs" in the sweat ducts.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. An anhydrous personal care composition for application to the skin or hair comprising a cosmetically acceptable, anhydrous carrier and zinc X halide complex precursors wherein the precursors are a zinc ion source, an X source, and a halide source, wherein the halide source can be part of the zinc ion source, the X source, or a halogen acid, wherein the precursors can complex into the zinc X halide when the composition is applied to the skin or hair, wherein X is lysine, and wherein the precursors are present in amounts such that when combined into the zinc X halide complex, the zinc X halide complex would be present in an amount of 0.05 to 10% by weight of the composition;
wherein the zinc X halide complex formed from the precursors is a zinc lysine chloride complex having the formula ZnLysine$_3$Cl$_2$.

2. The personal care composition according to claim 1 wherein the zinc ion source is selected from the group consisting of zinc oxide, zinc chloride, tetrabasic zinc chloride, zinc carbonate, zinc nitrate, zinc citrate, and zinc phosphate.

3. The personal care composition according to claim 1 wherein the precursors are zinc oxide with an amino acid hydrohalide.

4. The personal care composition according to claim 1 wherein the precursors are tetrabasic zinc chloride with lysine or lysine hydrohalide.

5. The personal care composition according to claim 1, wherein a total amount of zinc present in the composition is 0.05 to 8% by weight.

6. The personal care composition according to claim 1, wherein the zinc ion source is present in an amount of 0.05 to 10% by weight of the composition.

7. The personal care composition according to claim 1, wherein the X source is present in an amount of 0.05 to 30% by weight of the composition.

8. The personal care composition according to claim 1 wherein the zinc X halide formed from the precursors is ZnLysine$_3$Cl$_2$ having a structure wherein the zinc atom is located in an octahedral center coordinated with two oxygen and two nitrogen atoms in the equatorial plane coming from two lysine carboxylic acid and amino groups, respectively, with the zinc atom coordinated to the third lysine via its nitrogen and carboxylic oxygen located at the apical positions of the zinc center geometry.

9. The personal care composition according to claim 1 wherein the zinc X halide is formed in situ after the composition is formulated.

10. The personal care composition according to claim 1 wherein the cosmetically acceptable carrier comprises one or more ingredients selected from the group consisting of water-soluble alcohols; glycols; glycerides; medium to long chain organic acids, alcohols and esters; surfactants; additional amino acids; structurants; emollients; fragrances; and colorants.

11. The personal care composition according to claim 1 wherein the composition is an antiperspirant and/or a deodorant.

12. The personal care composition according to claim 1 wherein the composition is a body wash, a shower gel, a bar soap, a shampoo, or hair conditioner.

13. A method of reducing sweat and/or body odor comprising applying the composition of claim 1 to skin.

14. A method of killing bacteria comprising contacting the bacteria with a composition of claim 1.

15. A method of forming a zinc X halide comprising applying the composition according to claim 1 to skin or hair.

* * * * *